United States Patent

Nonaka et al.

[11] Patent Number: 6,094,760
[45] Date of Patent: Aug. 1, 2000

[54] BED SYSTEM FOR RADIATION THERAPY

[75] Inventors: Hideki Nonaka; Toru Kan, both of Niihama, Japan

[73] Assignee: Sumitomo Heavy Industries, Ltd., Tokyo, Japan

[21] Appl. No.: 09/128,469

[22] Filed: Aug. 4, 1998

[30] Foreign Application Priority Data

Aug. 4, 1997 [JP] Japan ..................... 9-209217
Mar. 5, 1998 [JP] Japan ..................... 10-053282

[51] Int. Cl.[7] .................................... A61G 13/00
[52] U.S. Cl. ........................ 5/601; 5/608; 5/600; 5/610
[58] Field of Search ............... 5/601, 600, 607, 5/608, 610, 611; 378/209, 193, 195, 196, 198; 600/410, 437

[56] References Cited

U.S. PATENT DOCUMENTS 5,013,018  5/1991  Sicek et al. ..................... 5/601
5,014,292  5/1991  Siczek et al. .................... 5/601

*Primary Examiner*—Terry Lee Melius
*Assistant Examiner*—Frederick Conley
*Attorney, Agent, or Firm*—Arent Fox Kintner Plotkin & Kahn, PLLC

[57] ABSTRACT

In a treatment bed system for radiation therapy a rotation drive mechanism (relative isocentric rotation drive mechanism, rolling rotation drive mechanism, and pitching rotation drive mechanism) for rotating the bed independently around three axes (i, r, and p) perpendicular with respect to a patient each other and a parallel transfer mechanism (X-axis direction transfer mechanism, Z-axis direction transfer mechanism, and Y-axis direction transfer mechanism) for transferring the bed independently in parallel in the directions of three axes (X, Z, and Y) perpendicular with respect to a floor surface each other are provided. Thereby, the irradiation from arbitrary directions and distances to a patient held stationary on the bed can be performed.

13 Claims, 15 Drawing Sheets

| IONIZATION MAGNITUDE | SMALL | LARGE |
| --- | --- | --- |
| PROTON SPEED | FAST | SLOW |
| INTERACTION TIME | SHORT | LONG |

BED SYSTEM FOR RADIATION THERAPY

BACKGROUND OF THE INVENTION

1. Field of the Invention

The present invention relates to a bed system for radiation therapy including a bed for holding a patient stationary when treatment is performed by applying radiation irradiated from an irradiating section to a diseased part, and more particularly to a bed system for radiation therapy which is suitable for use in a proton radiation therapy device having a rotation irradiation chamber (referred to as a gantry) and can achieve irradiation from any direction and distance, especially non-complanar irradiation whose irradiation direction is not perpendicular to the patient axis, to a patient held. stationary on a bed.

2. Description of the Prior Art

Conventional cancer therapy based on radiation of active rays uses X-rays, gamma rays, electron beams, fast neutron beams, etc. These active rays, as shown in FIG. 14, become the strongest at sites close to the surface of a patient, and thus may inflict damages on normal tissues close to the body surface when those rays are directed towards a cancer in a deeper part of the body. By the way, a proton or a particle which comes into being when a hydrogen atom has been removed of the electron, has a positive charge, and has a mass 1836 times as large as that of electron, can be accelerated under a high energy state by an accelerator to give a proton beam. The proton beam is characterized by having the maximum dose peak or a Bragg peak P at a certain depth from the body surface, and then declining rapidly to zero.

This is because, as the electric force a proton exerts on electrons becomes large in proportion to its proximity to the latter, when the proton has a high kinetic energy and runs at a high speed, the time for the proton to interact with nearby electrons is short, and ionization is small in magnitude, but, when it loses the kinetic energy to nearly make a stop, the time for interaction becomes long and ionization rapidly increases in magnitude.

Thanks to this nature peculiar to protons, it is possible to apply proton beams for cancer therapy keeping normal cells other than a cancer comparatively free from damages, even if the cancer lies in a deeper part of the body. Further, as the radiation-based biological effect (RBE) of a proton beam is nearly equal to that of X-rays, the proton radiation therapy is advantageous in that it can make the most of knowledge and experience accumulated in the field of conventional X-ray radiation therapy. With these features, the proton radiation therapy device is being introduced as a therapy means to treat a cancer without removing any functional organs and encroaching on the quality of life.

Such a proton radiation therapy device is generally constituted of a therapy device A, an attachment B, and an attendant facility device C, as shown in FIG. 15.

The therapy device A consists of, for example, a proton beam accelerator 1 which accelerates protons, changes the energy of the proton beam taken out, and limits the energy from being expanded, a beam transport system (BTS) 2 which secures a stable orbit for the proton beam to transport it to an irradiation chamber without loss, and a rotation irradiation device (gantry) 3 and a stationary irradiation device 4 which form and process the proton beam to irradiate it to a lesion position of a body exactly.

The proton beam accelerator 1 is composed of, for example, a cyclotron which is the main body of an accelerator and accelerates protons to an energy of 235 MeV and an energy selection system (ESS)which changes the energy of the proton beam irradiated from the cyclotron, if desired, while limiting the energy dispersion.

The rotation irradiation device 3 is composed of an irradiating section (nozzle) which realizes irradiation requirements such as an irradiation field and irradiation depth, a terminal section of the beam transport system (BTS) 2 which transports the beam to an entrance of the irradiation section, and a structure in which the nozzle and the terminal section of the beam transport system 2 are installed and which irradiates the beam in any direction from the nozzle attached to its tip, and a bed system including a positioning device for diseased part of a patient is located adjacent to the rotation irradiation device 3.

The stationary irradiation device 4 is substantially identical to the rotation irradiation device 3, but it is different from the rotation irradiation device 3 that proton beam irradiated from the nozzle are fixed only, for example, in the horizontal direction.

The attachment B comprises a diagnostic device, a therapy planning system for planning a irradiation therapy, and a therapy implement machine tool. The diagnostic device consists of an MRI and CT scanner for acquiring diseased part information in a body of a patient and an X-ray simulator for confirming the positioning of the diseased part in the body. The therapy planning system is composed of hardware and software for achieving the irradiation therapy planning according to the diseased part information in the body obtained from the diagnostic devices. The therapy implement machine tool is constituted of an NC electric discharge machine, NC machining center, and NC three-dimensional coordinate measuring instrument which process a patient collimator and bolus with on-line according to the output from the therapy planning system. Incidentally, the attachment B goes out the subject matter of the present invention and will not be discussed any further.

The attendant facility device C is composed of a various power sources in which the main components are DC current sources supplying power to the accelerator and the beam transport system and a pure water cooling and supplying facility for directly cooling an electric current conductor (coil). Incidentally, the attendant facility device C also goes out the subject matter of the present invention and will not be discussed any further.

The proton beam therapy device makes the safety to the patient and medical staff to the top priority from a viewpoint that it is a medical device, but on the other hand its safety, operability and easy maintenance are pursued as it is operated with a few people under the initiative of the medical staff. The system adopts a cyclotron as an accelerator and when compared with other types of accelerators the beam generated from the cyclotron has the following property:

(1) Large maximum electric current can be obtained (maximum 300 nA),
(2) The short time fluctuations of its electric current value and the beam shape are very small,
(3) The time fluctuation of the irradiation position of a beam is very small, and
(4) Various structures from continuous beam to pulse beam can be formed in time structure.

Furthermore, the cyclotron has the following referred characteristics other than the beam properties, that is, the cyclotron adopts a simple configuration in which only three devices are adjustment object devices in regular operation of the accelerator and also it is less prone to affect the performance of an MRI and CT simulator which are susceptible to the rapid fluctuation of magnetic field as the cyclotron is provided with a constant magnetic field unlike other accelerators which produce fluctuation of magnetic field and high frequency positively. These characteristics of the cyclotron results in the following features to the proton beam therapy device:

(1) The accelerator itself can perform the irradiation for therapy in a temporally and spatially stable condition, so that the system after the accelerator is made to be simplified and reliable (for example, if an irradiation field is less than 20 cm in diameter, a structurally simple and stable dispersion method can be employed), (2) An appropriate irradiation can be performed without restraining a patient for a long time according to the position of a diseased part fluctuating with breath of the patient regularly and irregularly, (3) It is provided with a capability sufficiently corresponding to a three-dimensional irradiation which will become an ideal irradiation form in the near future as a therapy irradiation, (4) The starting-up and shut-down time of the irradiation is short, a lot of time available for therapy can be produced, the operation is simple, and operators with knowledge and experience of an accelerator are not needed, and (5) The countermeasure against noise resulting from magnetic and high frequency fluctuation to medical electronic devices can be performed easily.

From the viewpoint of the whole proton beam therapy device, devices around an irradiation therapy section to which patients and medical staffs have to gain access daily are more important than the accelerator judging from securing safety and exerting irradiation and operation performance. The configuration around the irradiation therapy section is composed of, as described above, the irradiation device and the positioning device of a patient, and it is necessary to prioritize securing safety especially for these devices.

As for safety, basically to make the idea of fail-safe thorough, it is incontestable not only to implement the safety policy to device itself, such as mechanical safety design for an electrical machine and selection of materials for preventing radiation deterioration, but also to embody measures for patients and medical staffs, assuming various cases. For example, only to secure safety to the patient, it is necessary to assume various accidents and to embody safety measures, such as prevention of excessive dose irradiation exceeding a predetermined dose, prevention of mechanical trouble accidents caused by gantry structure drive, picture tube drive, and bed drive, securing safety emergency evacuation of patient when a device accident occurs, obviating the urgent fall when a collimator for patient and a bolus are exchanged, and accident detection of a patient and safety urgent countermeasure when irradiation is performed.

The function required for around the irradiation therapy section is to irradiate diseased parts as an irradiation condition created using the therapy planning system, that is, to irradiate proton beam within an allowable error so that the dose distribution and dose value to the diseased part of an irradiation object as planned may be obtained. In order to achieve the irradiation, it is required that the irradiation position of patient's diseased parts to a beam must be determined with sufficient accuracy and the dose distribution planned must be realized accurately using various instruments for beam formation arranged in the nozzle.

In order to satisfy the former requirement, the positioning of a patient's diseased part is performed with a procedure to carry out a precise positioning such that a beam axis and an irradiation center of the diseased part are, at first, made coincide with a criterion marking on a body surface of the diseased part using cross laser pointers arranged in the nozzle and an irradiation space to perform a coarse positioning in the horizontal and vertical directions, and subsequently, a precise positioning is performed by moving a bed so that the X-ray image information in the horizontal and vertical directions of the patient's diseased part obtained from a DRR (Digital Radiography Reconstruction) device disposed in an in radiation space and performing image reconstruction due to electronic signals is brought into agreement with the irradiation position set up in the therapy planning. In addition, as a prerequisite for the precise positioning, it is required that the positional accuracy including the reproducibility of the beam axis (nozzle) and the irradiation center position should be secured sufficiently.

Most of the requirement for the dose distribution of the latter may be solved basically if the beam property including the reproducibility is sufficiently stable temporally and spatially within the representative therapy time, and the latter part is dependent on how the measurement of dose distribution prior to the irradiation therapy using a phantom comprising water or the like derivative the absorption of a human body can be executed precisely and in a short time.

In the radiation therapy of cancer, it is ideal to concentrate a lethal dose of active rays onto the cancer alone without inflicting any irreversible damages to nearby normal tissues. The Proton radiation therapy, as shown in FIG. 14, exploits the feature characteristic with protons that a proton beam incident on a substance gives the maximum dose or Bragg peak P just before it ceases to move. Namely the therapy in question aims at achieving this ideal by covering only the cancerous lesion with that Bragg peak.

By the way, protons obtained from an accelerator are in the form of a slender beam, and its energy is constant (the depth of Bragg peak is also constant). On the other hand, cancerous lesions are varied in size and have complex shapes, and their depths in the body are not constant. Further, the density of tissues through which a proton beam must pass is not constant neither. Accordingly, to achieve an effective radiation therapy, it is necessary to (1) enlarge the proton beam to have a sufficient width to cover the whole cancer lesion in one radiation; (2) adjust the beam energy according to the depth of lesion; (3) give a sufficient energy distribution in depth so that the whole cancer lesion having a certain depth can receive a uniform irradiation; and (4) make corrections according to the irregularities in contour of the lesion, and in density of the tissues through which the proton beam must pass.

It is necessary to irradiate the proton beam adjusted according to the shape and depth of cancer to the cancer tissues inside of a patient correctly as the irradiation condition so that the expected dose distribution and dose value can be achieved within the allowable error.

In order to achieve such irradiation, it is necessary to decide the irradiation position of the patient to the beam precisely as well as to realize the dose distribution planned precisely using such a irradiation field forming device as a bolus or collimator.

In a proton beam therapy device described above, proton beam with high quality is produced from the cyclotron as an accelerator and also the position accuracy including the reproducibility of the positions of the beam axis (nozzle) and the irradiation center can be secured sufficiently in the proton beam irradiated from the nozzle in the direction of the patient, so that a bed used as a treatment table which moves the diseased part of the patient to be positioned has to be provided with a positioning drive means which allows the diseased part to be positioned by moving a human body having a weight of several tens of kg and being like a soft water bag as compared with solid material like a stone to the position in which the proton beam emitted from the nozzle exerts the maximum efficiency quickly and exactly with the minimum delay depending to an inertial force. Furthermore, in the case of disaster, such as earthquake or the like, the radiation of the proton beam must be stopped promptly and also the bed with a patient must be fixed at a predetermined position.

However, a conventional bed used in radiation therapy has only functions such that the bed with a patient held stationary can be inserted into an irradiation chamber in the direction of one axis and the irradiating section can be rotated around the axial center of the patient, so that the bed was not able to realize an irradiation from arbitrary directions and distances required in the radiation therapy, especially, a non-complanar irradiation in which the irradiation direction was not perpendicular to the axial center of the patient.

SUMMARY OF THE INVENTION

The present invention was performed to solve the above described problems, so it is an object of the present invention to achieve an irradiation to a patient held stationary on a treatment bed from arbitrary directions and distances, especially, to achieve a non-complanar irradiation.

It is another object of the present invention to provide a bed holding a patient stationary which can be transported to any position within a predetermined space, whose direction can be set up freely and in which positioning to its set up position can be performed for a long time, and in which brakes are made to be applied to the portions supporting the bed for unexpected vibration such as earthquake.

According to the present invention, in a bed system for radiation therapy including a bed for holding a patient stationary when a radiation therapy is performed by applying the radiation irradiated from an irradiating section to a diseased part, the bed system is provided with a rotation means for rotating the bed independently around three axes perpendicular with respect to the patient each other and a parallel transfer means for transferring the bed independently in parallel in the directions of three axes perpendicular with respect to a floor surface each other in order to solve said first object.

In addition, a center of said rotation may be placed in the irradiation chamber when the bed is inserted from outside of the irradiation chamber into inside of the irradiation chamber.

The rotation means may be composed of a hinge stand provided with a rolling rotation drive means for rotating the bed about the central axis of the longitudinal direction of the bed, a bed pedestal provided with a pitching rotation drive means for rotating the end of the longitudinal direction of the bed supported on the hinge stand to incline the bed surface, and a bed platform for supporting the bed pedestal and provided with a relative isocentric rotation drive means for rotatably driving the bed pedestal in the direction of X-Y plane.

The rolling rotation drive means may be provided with a handle mechanism for rotating the bed manually about the central axis of the longitudinal direction of the bed.

The parallel transfer means may be constituted of a Y-axis slide table provided with a Y-axis drive means for driving the bed or the bed platform in the Y-axis direction of the back and forth directions from outside to inside of the irradiation chamber, a lift table provided with a Z-axis drive means for drive the Y-axis slide table in the Z-axis direction of the up and down directions, and a base provided with an X-axis drive means for driving the lift table in the X-axis direction of right and left directions.

Brake mechanisms may be provided between any of desired objects in the hinge stand, bed pedestal, bed platform, Y-axis slide table, lift table, and base and their supporting sections.

Furthermore, an acceleration sensor which detects acceleration generated in the direction of three dimensions may be provided in the bed and also there may be provided a control means which issues a drive command to the rotation means (rolling rotation drive means, pitching rotation drive means, and relative isocentric rotation drive means) and the parallel transfer means (Y-axis drive means, Z-axis drive means, and X-axis drive means) so that these drive means are to be driven in the direction which decreases the output of the acceleration sensor.

In addition, both of brake mechanisms by friction and fitting may be provided between the lift table and the base.

Any desired drive means in the rotation means (rolling rotation drive means, pitching rotation drive means, and relative isocentric rotation drive means) and the parallel transfer means (Y-axis drive means, Z-axis drive means, and X-axis drive means) may be driven with a negative feedback control which controls an instruction position and a present position so as to be always maintained in the same position.

According to the present invention, the irradiation to a patient held stationary on a treatment bed can be performed from arbitrary directions and distances, so that the irradiation with high accuracy can be executed to improve the therapy effect.

In particular, when the bed is provided with a handle mechanism which rolls the bed manually around the central axis of the longitudinal direction of the bed, the bed can be moved slightly with manual operation, so that the diseased part can be fine-tuned to the optimum position for irradiation.

In addition, when brake mechanisms are provided between any of desired objects in the hinge stand, bed pedestal, bed platform, Y-axis slide table, lift table, and base and their supporting sections, the brakes can be applied to the desired sections in each of the rotation parts and transfer parts, so that when an interruption of irradiation occurs and a service personnel enters the gantry during the adjustment time and unexpectedly collides against any part of the treatment table, no position displacement of the bed occurs, allowing resumption of the safe and exact radiation therapy.

Moreover, when an acceleration sensor which detects acceleration generated in the direction of three dimensions respectively is provided in the bed and also a control means which issues a drive command to the rotation means and the parallel transfer means so that these drive means are to be driven in the direction which decrease the output of the acceleration sensor, even when the bed tends to oscillate to some extent, the acceleration sensor catches the oscillation and drive the bed in the opposite direction of the oscillation direction, so that the bed can be maintained a constant position.

Additionally, when both brake mechanisms by friction and fitting are provided between the lift table and the base, a brake with friction is used in normal operation, but when the lift table suddenly starts moving to the base at the time of calamities, such as an accident or earthquake, a brake using fitting mechanism operates to fix the whole treatment table to the base, so that the treatment table does not slide on the base and destroy the drive mechanism or the like.

Alternatively, when any desired drive means in the rotation means (rolling rotation drive means, pitching rotation drive means, and relative isocentric rotation drive means) and the parallel transfer means (Y-axis drive means, Z-axis drive means, and X-axis drive means) is made to be driven with a negative feedback control which controls an instruction position and a present position so as to always maintain in the same position, the diseased part can be introduced to an appropriate position and also the position can be retained accurately for a long time.

BRIEF DESCRIPTION OF THE DRAWINGS

The preferred embodiments will be described below with reference to the drawings, wherein like elements have been denoted throughout the figures with like reference numerals, and wherein.

DESCRIPTION OF THE PREFERRED EMBODIMENTS

The present invention will hereinbelow be described in further detail with reference to the accompanying drawings.

Figure 1:
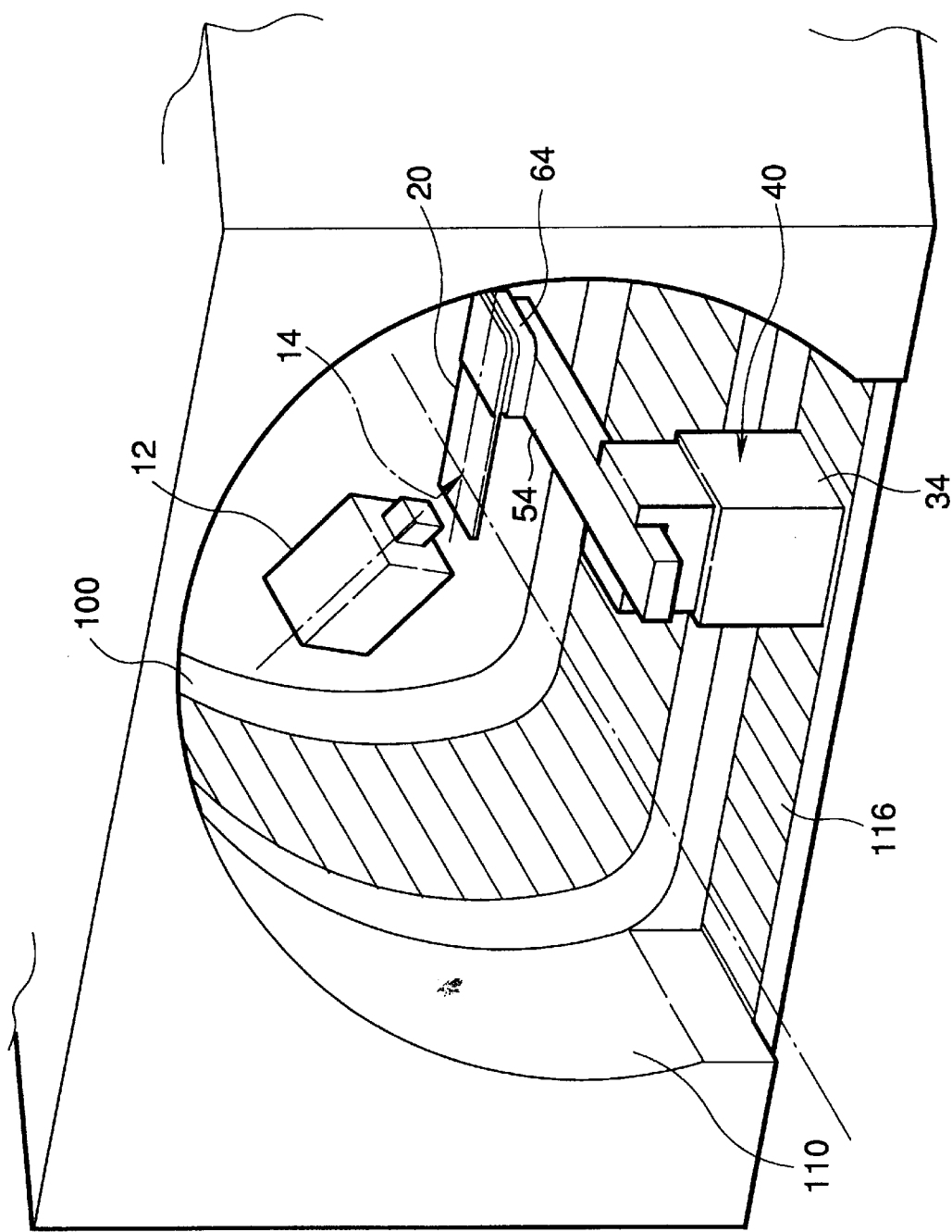
FIG. 1 is a perspective view showing the entire configuration according to the embodiment of the present invention.

Referring to FIG. 1, there is shown a proton beam therapy device according to the embodiment of the present invention which is equipped with a rotation gantry 100 in which an irradiating section 12 of a proton beam 14 is made rotatable around a treatment bed 20 holding a patient stationary.

Figure 2:
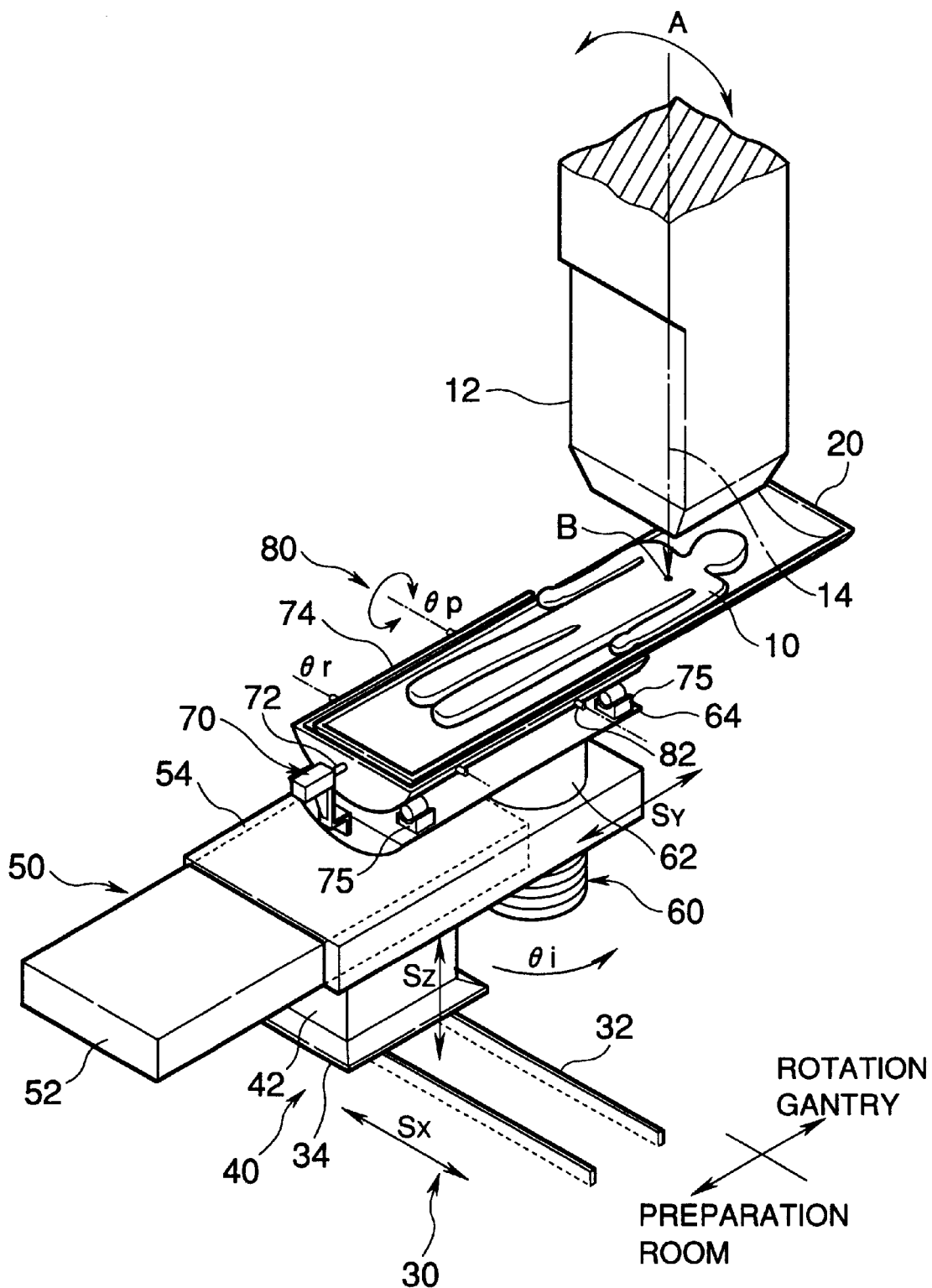
FIG. 2 is a perspective view showing an example of arrangement of the rotation gantry and the preparation room according to the first embodiment of the present invention.

In a treatment bed system including a bed 20 for holding a patient 10 stationary used when therapy is performed by applying a proton beam 14 irradiated from an irradiating section 12 to a diseased part, as shown in FIG. 2, a first embodiment according to the present invention is provided with an X-axis direction transfer mechanism 30 containing a slide base 34 movable in parallel on slide rails 32 fixed in a preparation room 110 side (refer to FIG. 1) in front of the rotation gantry 100 in order to make the bed 20 movable, as shown in FIG. 2 by arrow mark, in the horizontal direction Sx (transverse direction, referred to as X-axis direction) parallel to a plane including a rotation direction of the irradiating section 12, a Z-axis direction transfer mechanism 40 containing a lift stand 42 fixed on the slide base 34 in order to make the bed 20 movable in the vertical direction Sz (height direction, referred to as Z-axis) perpendicular to the X-axis direction, a Y-axis direction transfer mechanism 50 containing a bed platform 54 movable in the back-and-forth direction Sy of the direction from the preparation room 110 shown in FIG. 1 to the rotation gantry 100 (longitudinal direction, referred to as Y-axis) on a base plate 52 fixed to the upper part of the lift stand 42 in order to make the bed movable in the Sy direction, a relative isocentric rotation drive mechanism 60 attached in the vicinity of the tip in the gantry side of the bed platform 54 in order to enable the bed 20 θi rotation (referred to as relative isocentric rotation) around an isocentric axis (i-axis) 62 designating the height direction of a patient, a rolling rotation drive mechanism 70 which is disposed on a bed pedestal 64 fixed on the upper end of the i-axis 62 of the relative isocentric rotation drive mechanism 60 and enables the bed 20 θr rotation (referred to as rolling rotation) around a rolling axis (r-axis) designating the direction of axial center of a patient 10, and a pitching rotation drive mechanism 80 which is disposed on a rotation stand 74 rotated by the rolling rotation drive mechanism 70 and enables the bed 20 θp rotation (referred to as pitching rotation) around a pitching axis (p-axis) 82 perpendicular to the axial center of a patient 10.

In FIG. 2, B designates an irradiation center (referred to as an iso-center).

Figure 15:
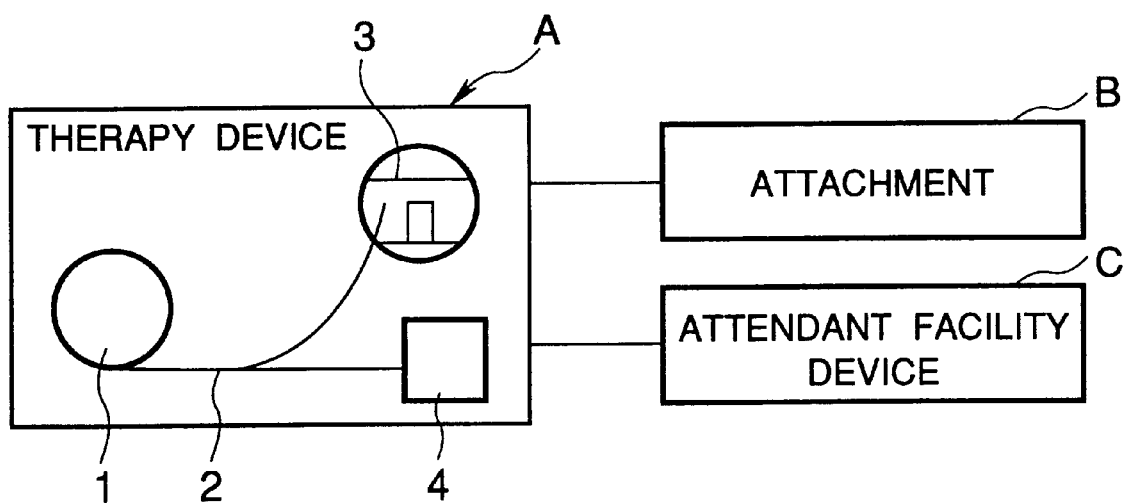
FIG. 15 is the entire configuration view of the proton beam therapy system.

The irradiating section 12 is enabled to be rotated and moved around the bed 20 along the inner periphery surface of the rotation gantry 100, as shown in FIG. 1. A proton accelerator 1 containing a cyclotron and energy selection system (ESS) which accelerates protons, changes the energy of proton beam taken out, and limits the energy from being expanded and a beam transport device 2 which secures a stable orbit of the proton beam produced in the proton accelerator 1 to transport it to the rotation gantry 100 with less loss are connected to the irradiating section 12, as shown in FIG. 15.

The i-axis 62 of the relative isocentric rotation drive mechanism 60 can be adjusted to any position by the Y-axis direction transfer mechanism 50 so that the i-axis 62 can be disposed with offset to a transfer center line (a center line 42C of the lift stand 42) of the Z-axis direction transfer mechanism 40, and can be disposed in the gantry 100.

Next, the operation according to the embodiment will be described.

When a therapy is performed to a patient, the shape of a therapy object organ, the posture at the time of therapy with consideration to depth and direction, and the direction and position of a nozzle from which the proton beam is radiated are calculated during the therapy simulation, and their position data are input to a control system of a patient positioning device using a coordinate system (for example, X, Y, and Z coordinate) convenient to the operator of the proton beam therapy device. As for the input data (positions and angles), coordinate conversion is performed as the positions of direction of X-axis, Y-axis, and Z-axis, the rotation angles of i-axis (relative isocentric rotation), p-axis (pitching rotation), and r-axis (rolling rotation), and the position of diseased part of the patient, and each of the axes of the bed receives the converted data as the input position data and drives each axis to transfer the diseased part of the patient to the desired position. When a posture of the patient obtained from the simulation is not appropriate, the posture of the patient may be fine-tuned.

Figure 3:
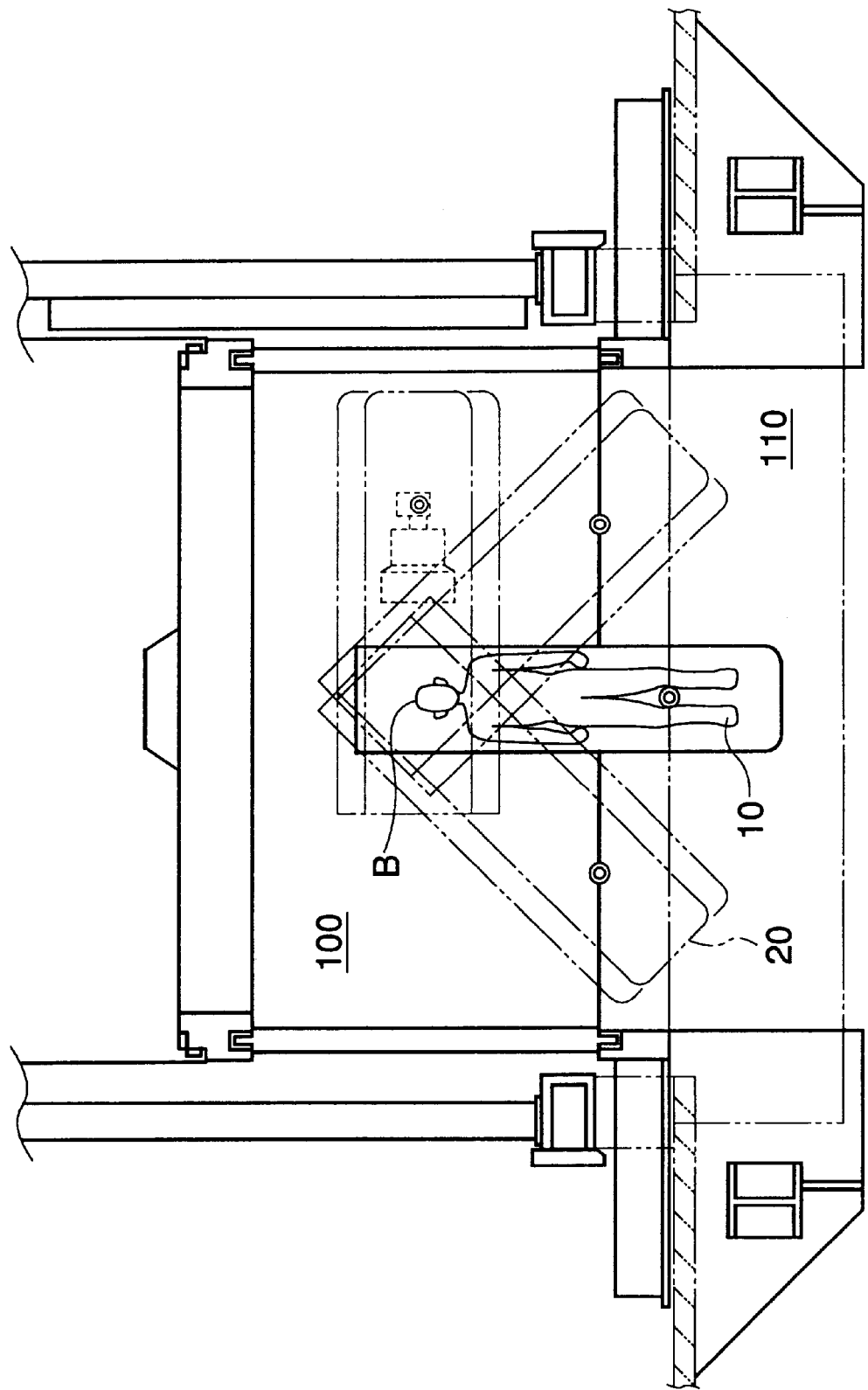
FIG. 3 is a plan view showing the irradiation condition to a patient according to the first embodiment.
Figure 4:
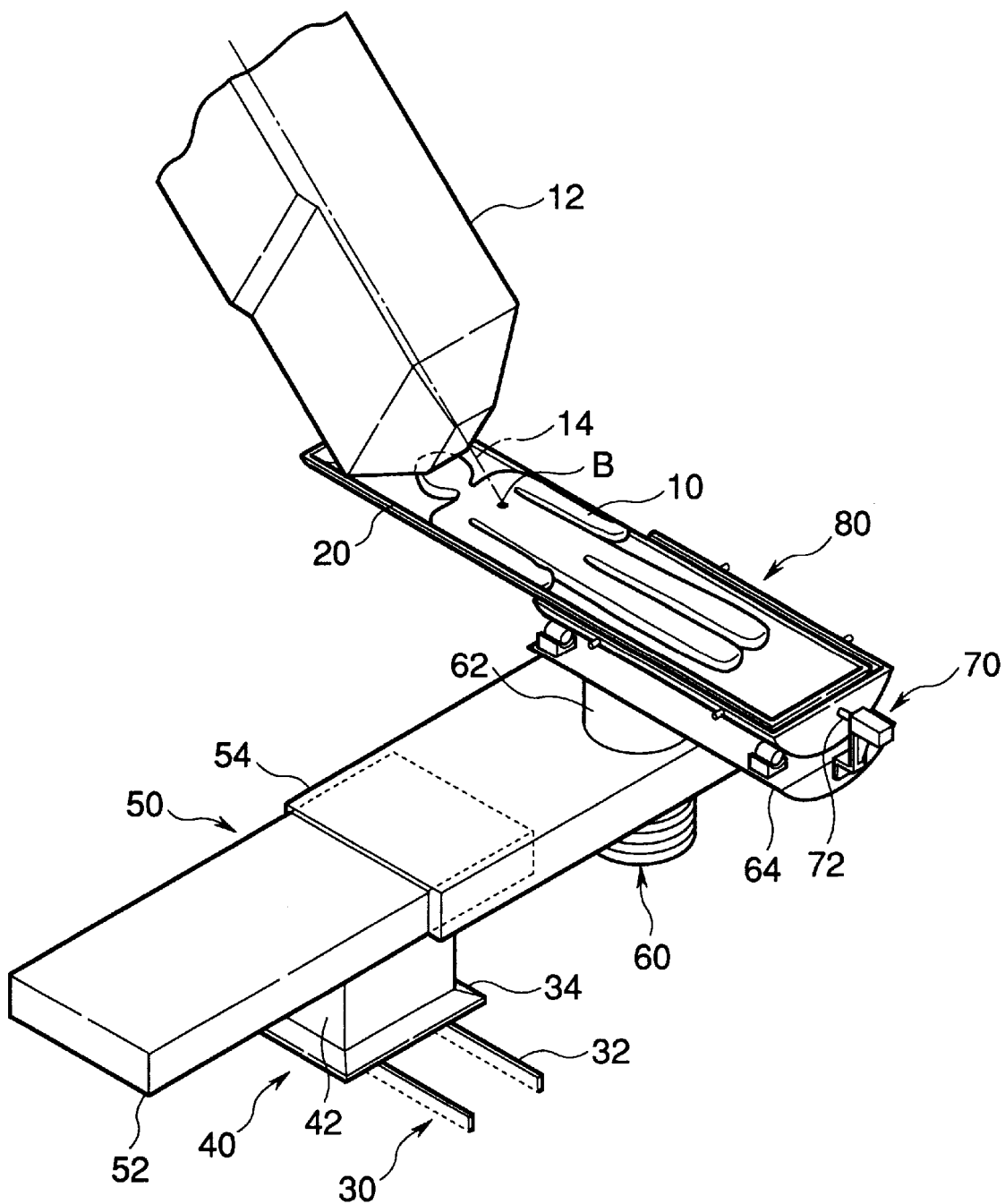
FIG. 4 is a perspective view showing non-complanar irradiation being executed to a patient according to the first embodiment.

FIG. 3 shows that the bed 20 is rotated around the iso-center B, and FIG. 4 shows that non-complanar irradiation is performed in which the irradiation direction is not right angle with respect to the axial center of the patient 10.

In the present embodiment, the i-axis 62 of the relative isocentric rotation is made to be offset with respect to the center line 42C of the lift stand 42 in the Z-axis direction transfer mechanism 40 to be disposed in the rotation gantry 100, so that the positioning with respect to the irradiating section 12 can be performed easily. Incidentally, the i-axis 62 can be placed outside of the rotation gantry 100.

A second embodiment of the present invention resulting from incorporating the first embodiment will be described in more details.

The second embodiment is provided with the X-axis direction transfer mechanism 30, Z-axis direction transfer mechanism 40, Y-axis direction transfer mechanism 50, the relative isocentric rotation drive mechanism 60, the rolling rotation drive mechanism 70, and the pitching rotation drive mechanism 80 similar to those of the first embodiment, and like parts are represented by like reference characters and their detailed explanation will be omitted.

Figure 5:
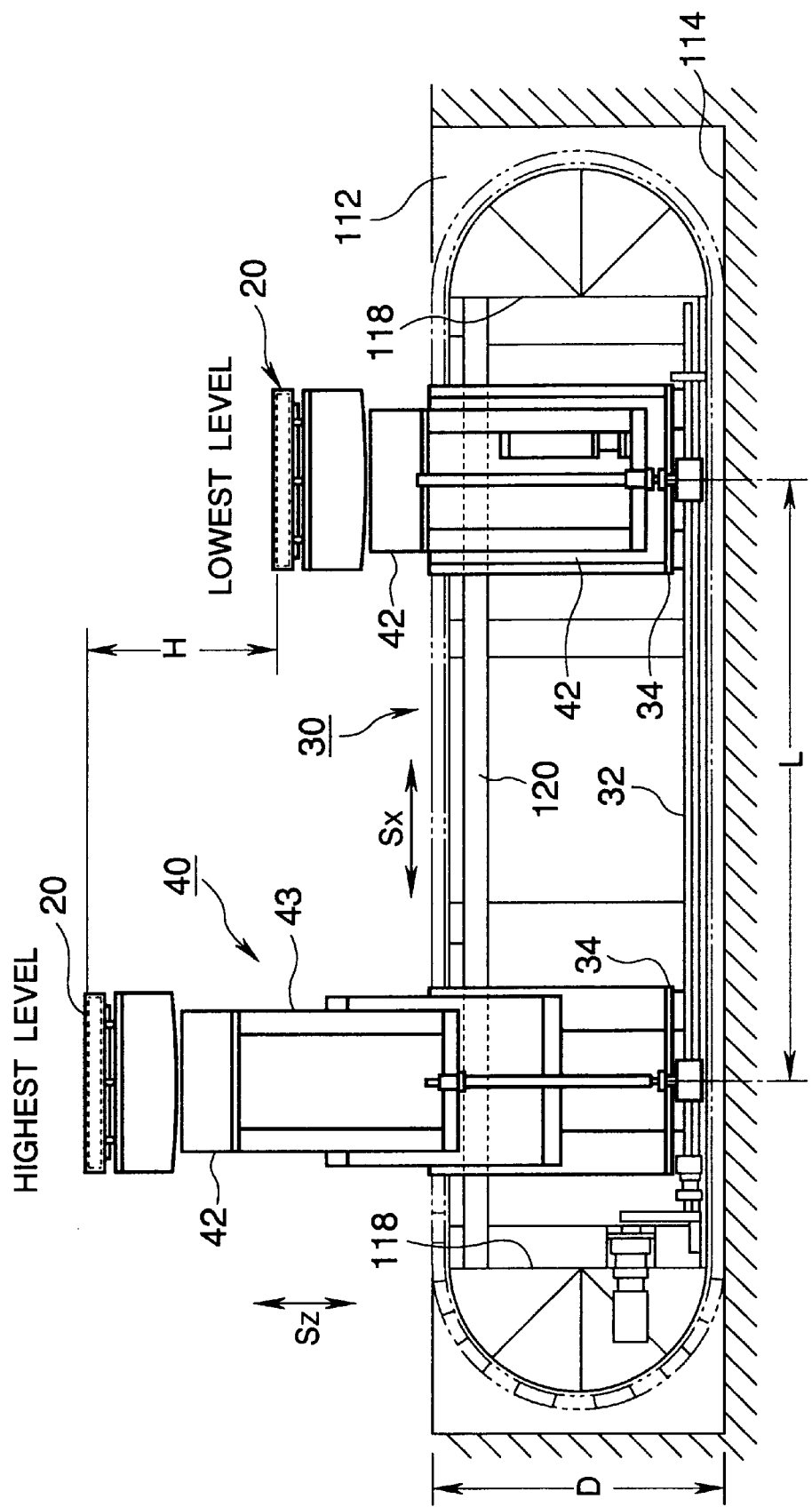
FIG. 5 is a transverse cross section showing the X-axis direction transfer mechanism and Z-axis direction transfer mechanism according to the second embodiment of the present invention.

The slide rails 32 of the X-axis direction transfer mechanism 30 according to the second embodiment, as shown in FIG. 5 in detail, are fixed to a bottom surface 114 of a pit 112 dug on the floor of the preparation room 110, thereby the sufficient transfer distance L in the X-axis direction is secured (in the present embodiment, L=2,200 mm). On the upper surface of the pit 112, there is provided a caterpillar-like access floor 116 (refer to FIG. 1) which is connected in an endless belt-like and transferred in the direction of Sx of the slide base 34 to allow patients and operators to access the rotation gantry 100 easily.

With reference to FIG. 5, reference numerals 118 are semilunar guide plates which switch the direction of the access floor 116 while holding both ends of the transfer direction, and reference numerals 120 are X-axis direction guide rails similar to slide rails 32 disposed on the upper part of the pit 112.

A stretch cylinder 43 for driving the lift stand 42 of the Z-axis direction transfer mechanism 40 according to the second embodiment in the Z-axis direction Sz of the vertical direction is constructed, as shown in FIG. 5 in detail, for example, with three-step type, and even when the depth D of the pit 112 is not so large, a sufficient Z-axis direction transfer distance H can be secured (in this embodiment, H=700 mm).

Figure 6:
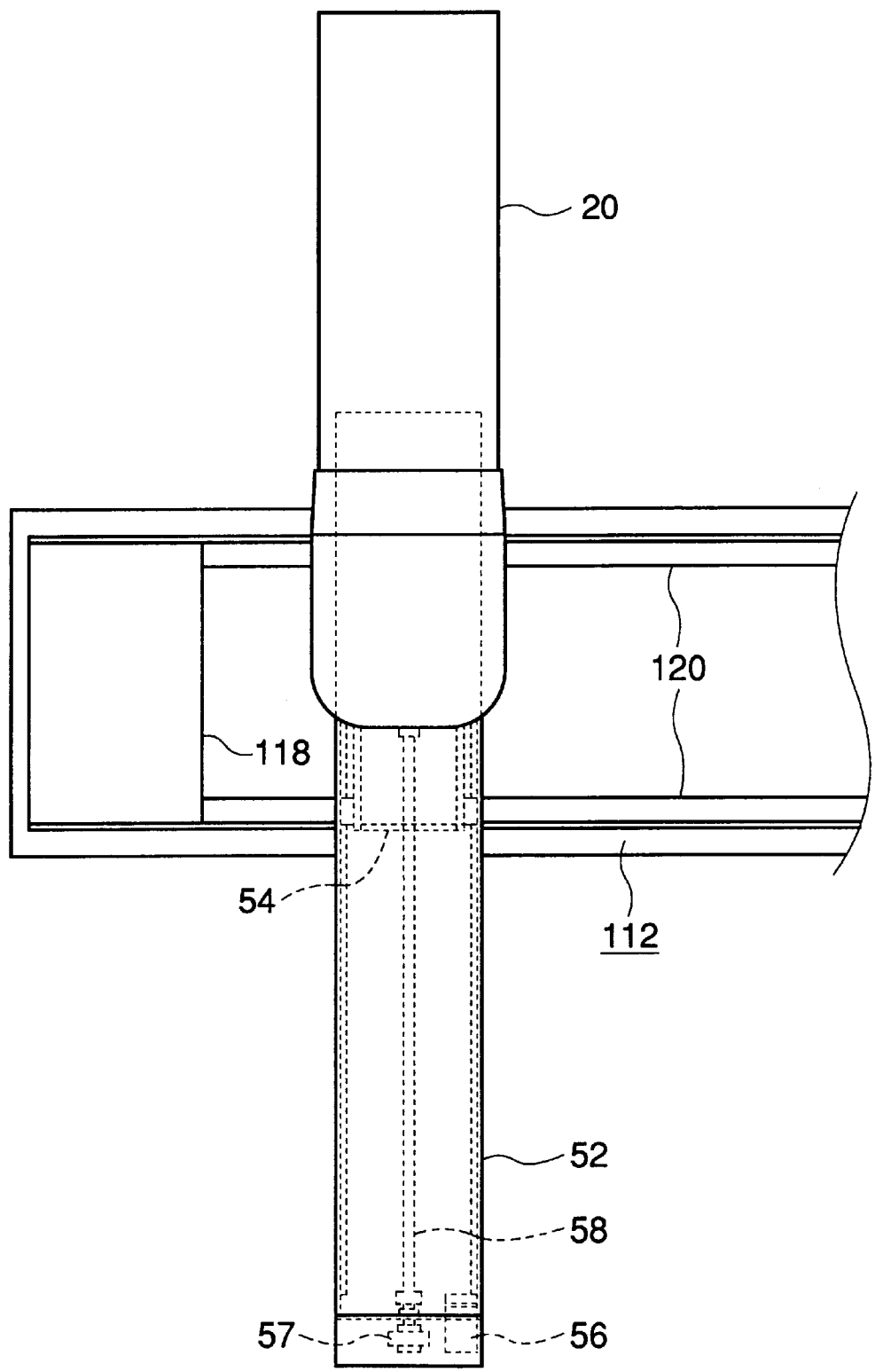
FIG. 6 is a plan view showing the Y-axis direction transfer mechanism according to the second embodiment.
Figure 7:
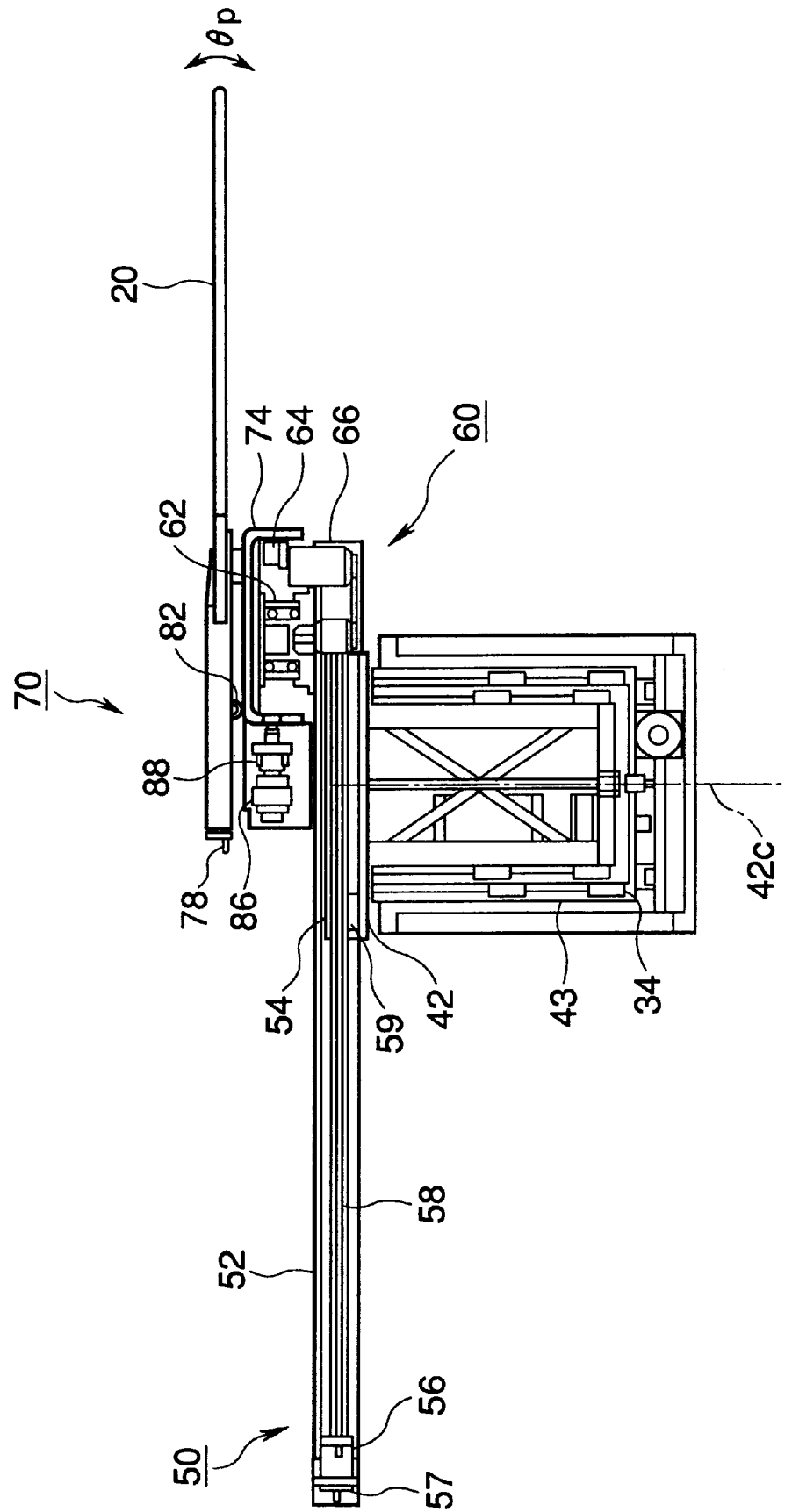
FIG. 7 is a vertical longitudinal cross section showing the rolling rotation drive mechanism and relative isocentric rotation drive mechanism according to the second embodiment.

The Y-axis direction transfer mechanism 50 according to the second embodiment is composed of, as shown in FIGS. 6 and 7 in detail, an electric motor 56 and torque limiter 57 disposed in the vicinity of the rear end inside of the base plate 52, a feed screw 58 driven by the motor 56, and a nut 59 fixed to inside of the bed platform 54 screwed to the feed screw 58, so that a sufficient transfer distance E (in this second embodiment, E=1,600 mm) in the Y-axis direction can be secured.

The relative isocentric rotation drive mechanism 60 according to the second embodiment is provided, as shown in FIG. 7 in detail, with an electric motor 66 for rotatably driving the bed pedestal 64 around the i-axis 62, so that sufficient isocentric rotation angles (in this second embodiment, ±90 degrees) can be obtained.

Figure 8:
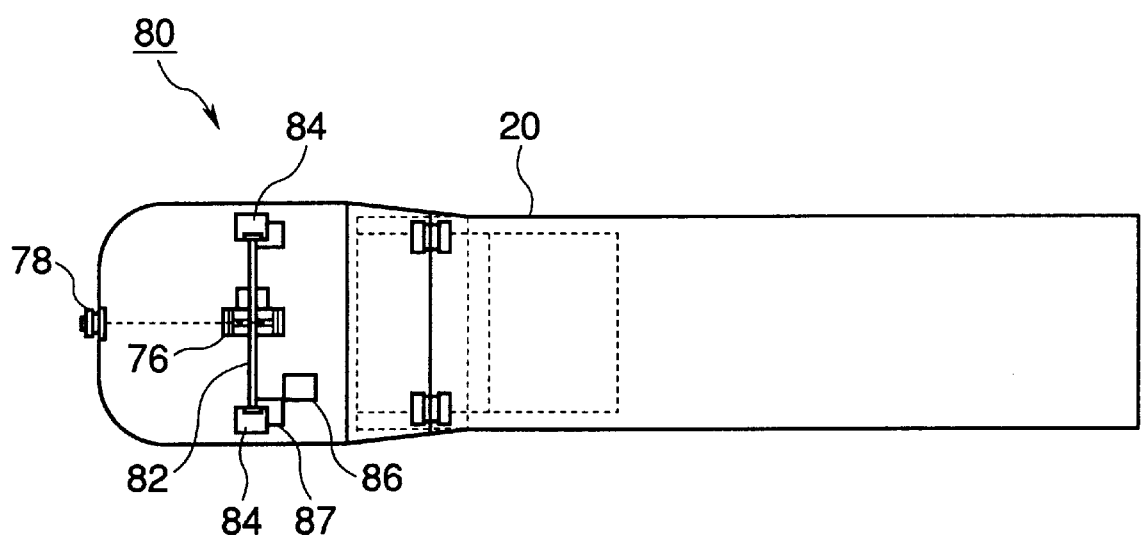
FIG. 8 is a plan view showing the rolling rotation drive mechanism and pitching rotation drive mechanism according to the second embodiment.
Figure 9:
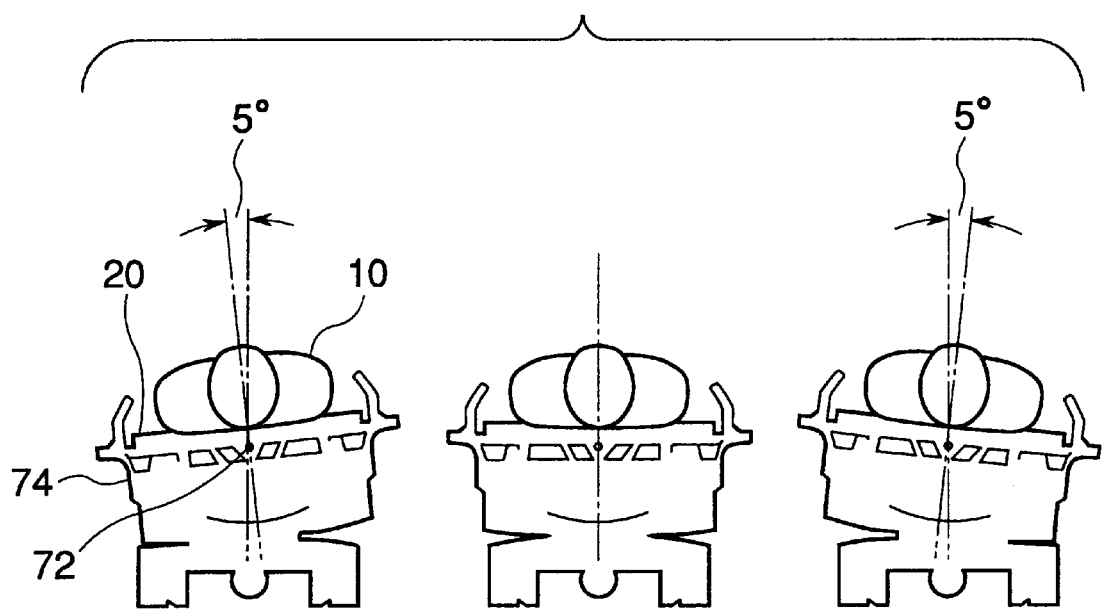
FIG. 9 is a transverse cross section showing the rolling rotation condition according to the second embodiment.

The rolling rotation drive mechanism 70 according to the second embodiment is composed of, as shown in FIGS. 7 and 8 in detail, a gear mechanism 76 and a manual handle 78 for making the bed 20 rolling rotation around the r-axis 72, so that, as shown in FIG. 9, it enables the bed 20 with a patient 10 rolling rotation around the r-axis 72 with sufficient rolling rotation angles (in this second embodiment, ±5 degrees).

Figure 10:
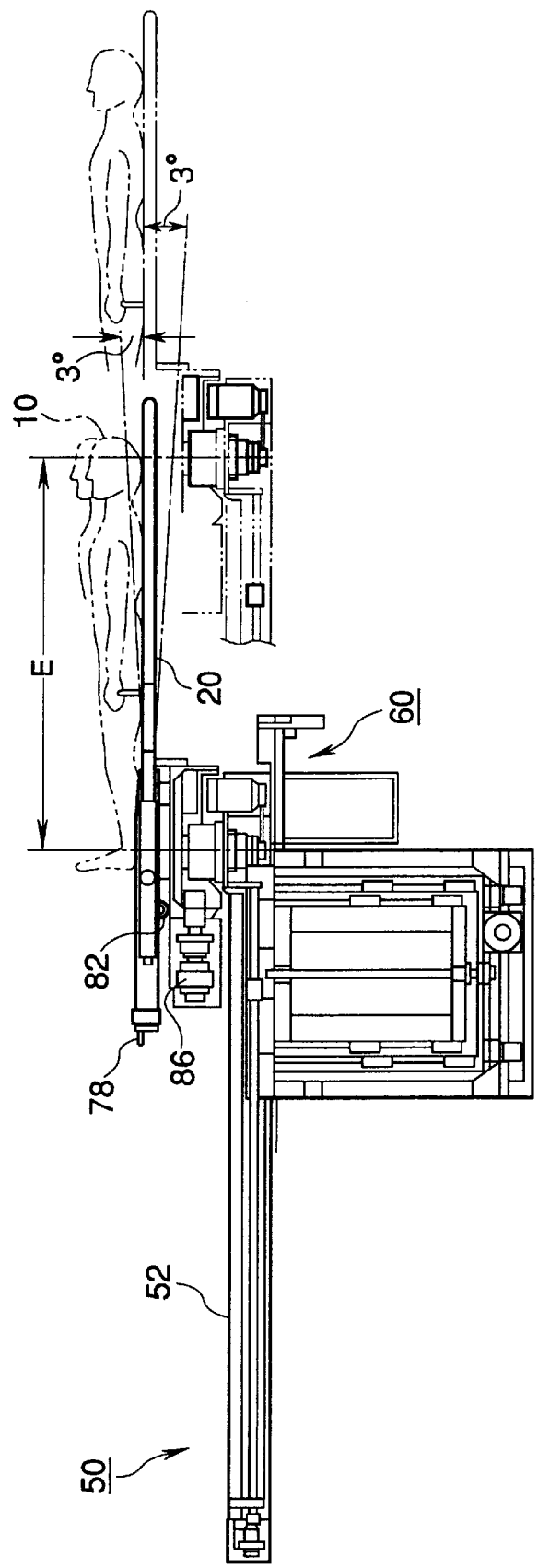
FIG. 10 is a vertical longitudinal cross section showing the rolling rotation condition according to the second embodiment.

The pitching rotation drive mechanism 80 according to the second embodiment is composed of, as shown in FIGS. 7, 8, and 10 in detail, an electric motor 86, a gear mechanism 87, and a torque limiter 88 for making the bed 20 pitching rotation around the p-axis 82 supported by a bearing 84 with sufficient pitching rotation angles $\theta p$ (in this second embodiment, $qp=\pm 3$ degrees).

Figure 11:
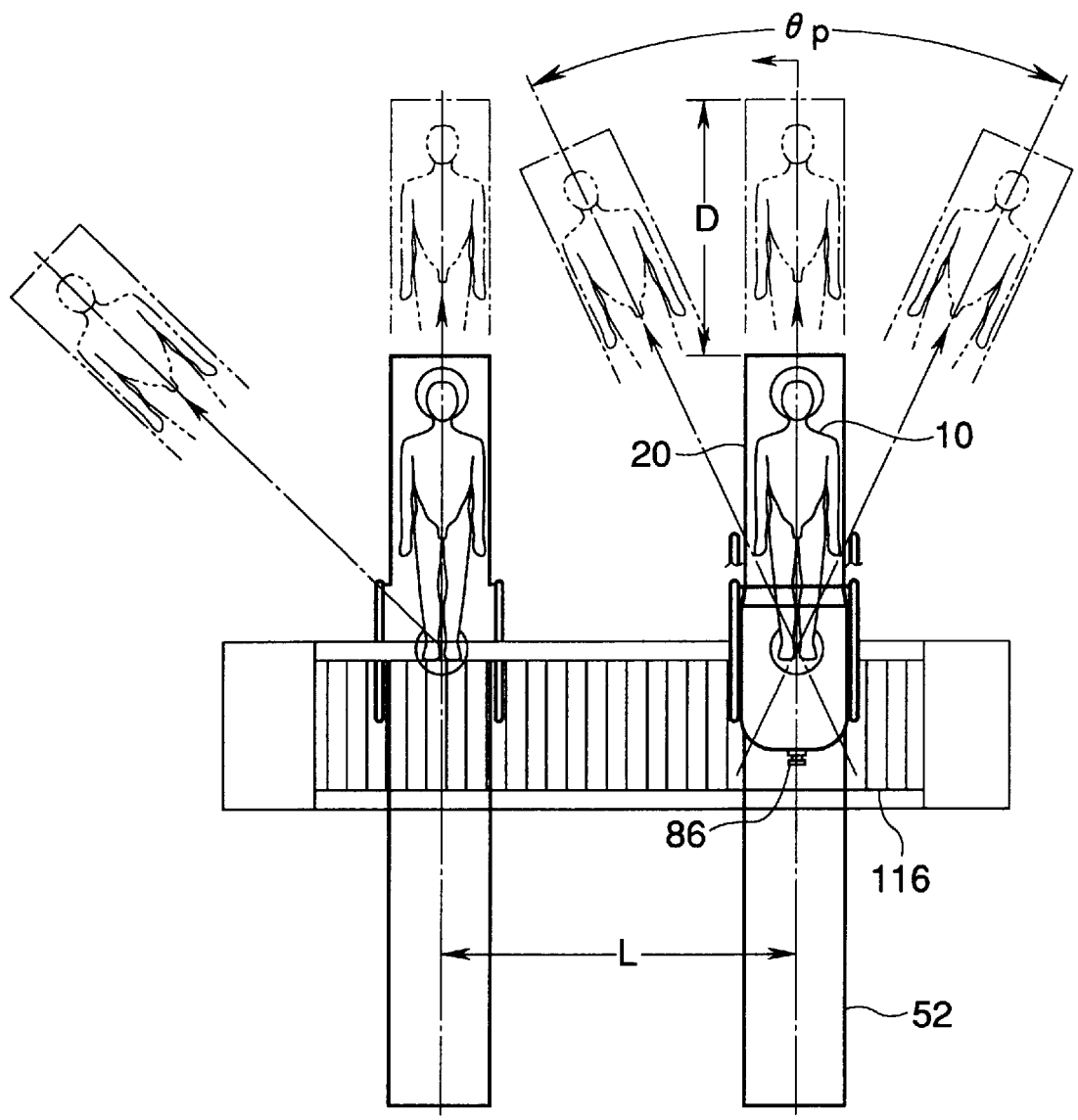
FIG. 11 is a plan view showing the irradiation condition to a patient according to the second embodiment.

A horizontal transfer condition of the bed 20 according to the second embodiment will be illustrated in FIG. 11.

A third embodiment according to the present invention will be described in detail below.

The third embodiment is also provided with the X-axis direction transfer mechanism 30, the Z-axis direction transfer mechanism 40, the Y-axis direction transfer mechanism 50, the relative isocentric rotation drive mechanism 60, the rolling rotation drive mechanism 70, and the pitching rotation drive mechanism 80 similar to those of the first and second embodiments, and like parts are represented by like reference characters and their detailed explanation will be omitted.

Figure 12:
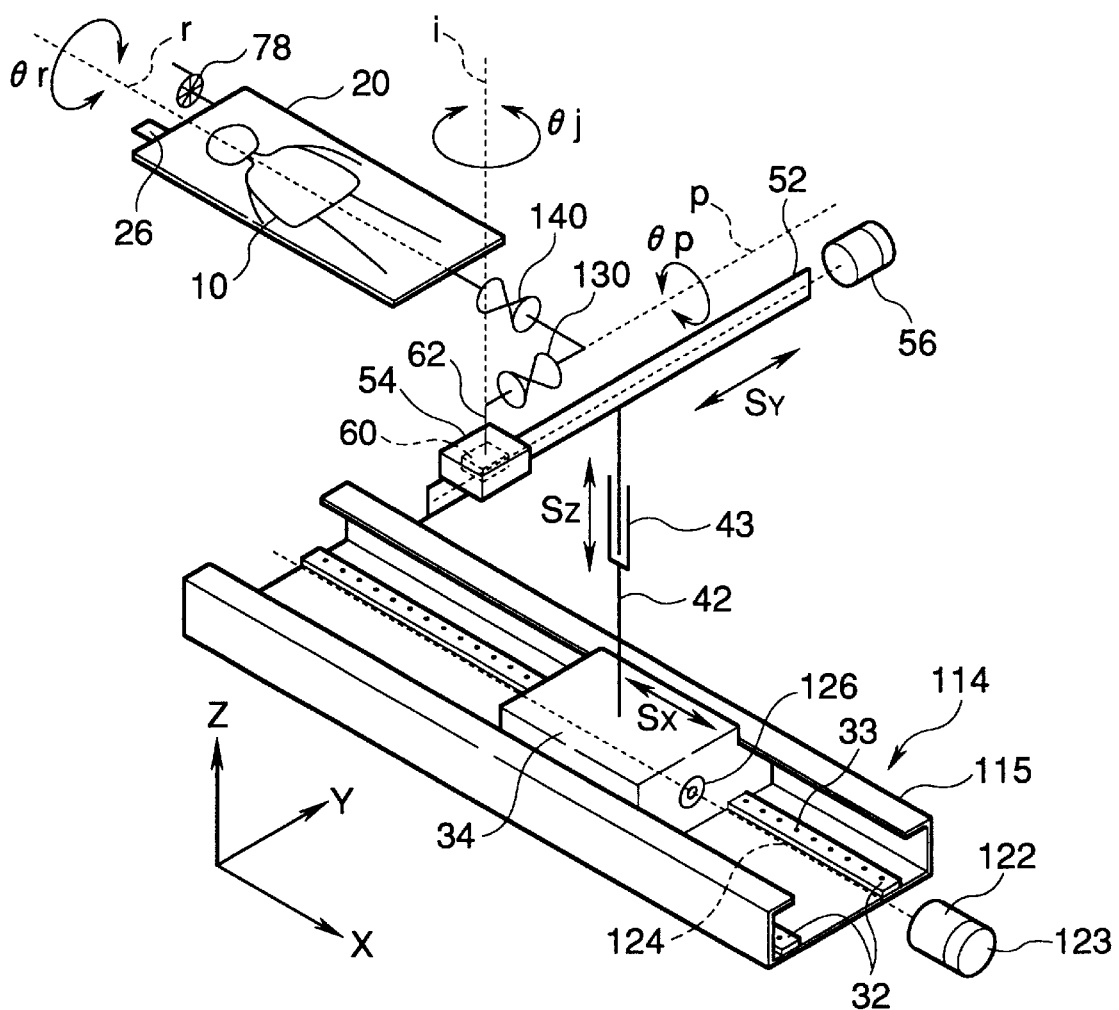
FIG. 12 is a perspective view showing the degree of freedom of the treatment table according to the third embodiment of the present invention.

FIG. 12 is a perspective view to help explain a degree of freedom of the bed 20 according to the third embodiment. The bed system is provided with a base 115 fixed to the floor surface 114. The base 115 is formed in elongated configuration and fixed to the floor surface in the direction of the X-axis. A slide base 34 is provided on the base 115 slidably in the X-axis direction. When examining the actual structure of the slide base 34, it is found that two slide rails 32 are laid down on the base 115 and a plurality of holes 33 are drilled for each several centimeters on the rails. Wheels rolling on the rails 32 are provided in the slide base 34, and the slide base 34 moves on the rails 32. In addition, brake shoes are provided in the slide base 34, and the brake shoes squeeze not the wheels but the rails 32 to fix the slide base 34 to the base 115. Incidentally, the brake mechanism may be provided with such structure that, as is known in the art, the slide base 34 is fixed to the rails by making the brake shoes to squeeze the periphery of the wheels. Furthermore, the slide base 34 is provided with a brake stick for emergency stop, and when the slide base 34 is shifted on the rails with abnormal condition by vibration caused by an accident or earthquake although the brake is under operation, an emergency brake is operated so that the brake stick is extruded to the rails 32 to be fitted into one of the holes 33, making the slide base 34 to be fixed on the rails 32.

A screw bar 124 rotated by a pulse motor 122 anchored to the base 115 is rotatably provided on the base 115, on the other hand, a ball screw 126 screwed to the screw bar 124 is attached in the slide base 34. Thus, when the pulse motor 122 is rotated by a position instruction signal sent from the positioning system holding a patient, the slide base 34 can be moved in the X-axis direction accurately in proportion to its rotation angles. In addition, when a pulse coder 123 which detects a relative movement to the base 115 is provided in the pulse motor 122 and a negative feedback control is performed to the relative movement to the base 115 of the slide base 34 using the detected amount of the pulse coder 123 as a feedback amount, the slide base 34 can be position controlled more accurately.

The lift stand 42 telescopical in the vertical direction is fixed to the slide base 34, which makes a Y-axis slide plate 52 attached to the tip of the lift stand 42 to be transferred vertically (in the Z-axis direction) by a vertical position instruction signal sent from the control system of the diseased part positioning device holding a patient. The lift stand 42 is theoretically a rigid structure and can be extended or retracted only in the vertical direction. Therefore, the lift stand 42 is actually a combination of an oar structure using a rigid steel skeleton construction in order to embrace an amount of deformation caused by vibration impact within a negligible range with regard to overall drive system, and those oars are combined into a socket and spigot joint structure to adjust the substantial height of the lift stand 42 by sliding these oars with each other according to a telescopical cylinder 43 driven by the pulse motor. Moreover, a position detector, for example, such as an inductosyn can be provided in the lift stand 42, and a height control with feedback similar to that of the slide base 34 can be performed based on vertical position signals obtained from the position detector described above. The slide sections each composed of socket and spigot joints in the lift stand 42 are provided with brake mechanisms, not shown in the figure in detail, so that the operation of the lift stand 42 can be fixed in the case of emergency.

The Y-axis slide plate 52 anchored to the tip of the lift stand 42 is formed in an elongated configuration in the Y-axis direction. The Y-axis slide plate 52 is disposed accurately in the Y-axis direction and is connected to the tip of the lift stand 42 at its central section. The Y-axis slide plate 52 is substantially a rigid structure. Rails similar to those on the base 115 are provided on the Y-axis slide plate 52, not shown in the figure, and the bed platform 54 is placed movably in the Y-axis direction on the rails. A brake mechanism is provided on the bed platform 54 and the Y-axis slide plate 52 can be stopped with regard to the Y-axis slide plate 52 in the case of emergency. A Y-axis position command signal sent from the control system of the diseased part positioning system holding a patient allows the bed platform 54 to be moved in the Y-axis direction. In addition, a position detector, for example, such as a inductosyn can be provided to detect a relative position to the Y-axis slide plate 52 of the bed platform 54, and a Y-axis control according to the feedback similar to that of the slide base 34 can be performed based on vertical position signals obtained from the position detector.

Figure 13:
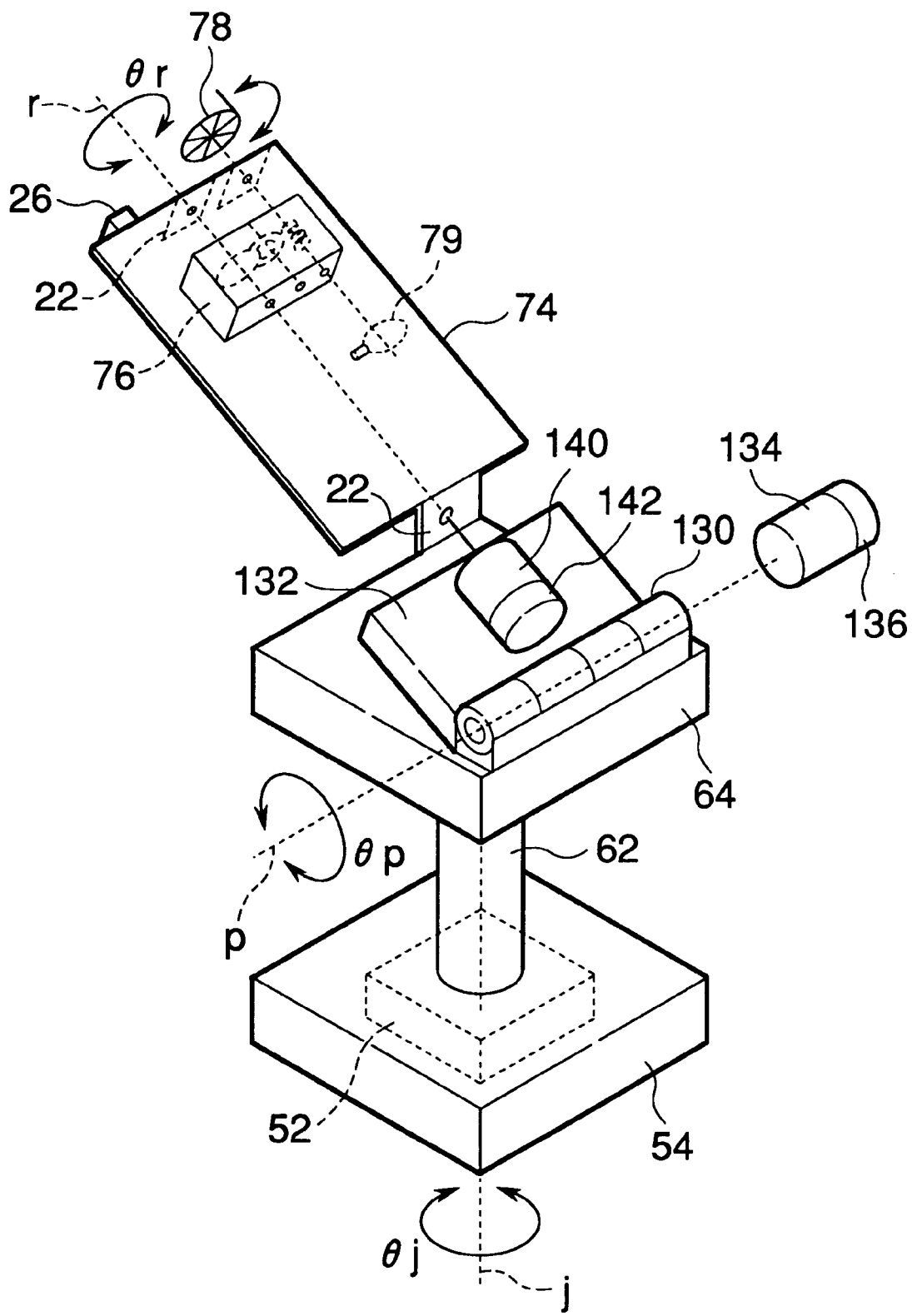
FIG. 13 is an enlarged perspective view showing the degree of freedom of the rotation drive mechanism according to the third embodiment.
Figure 14:
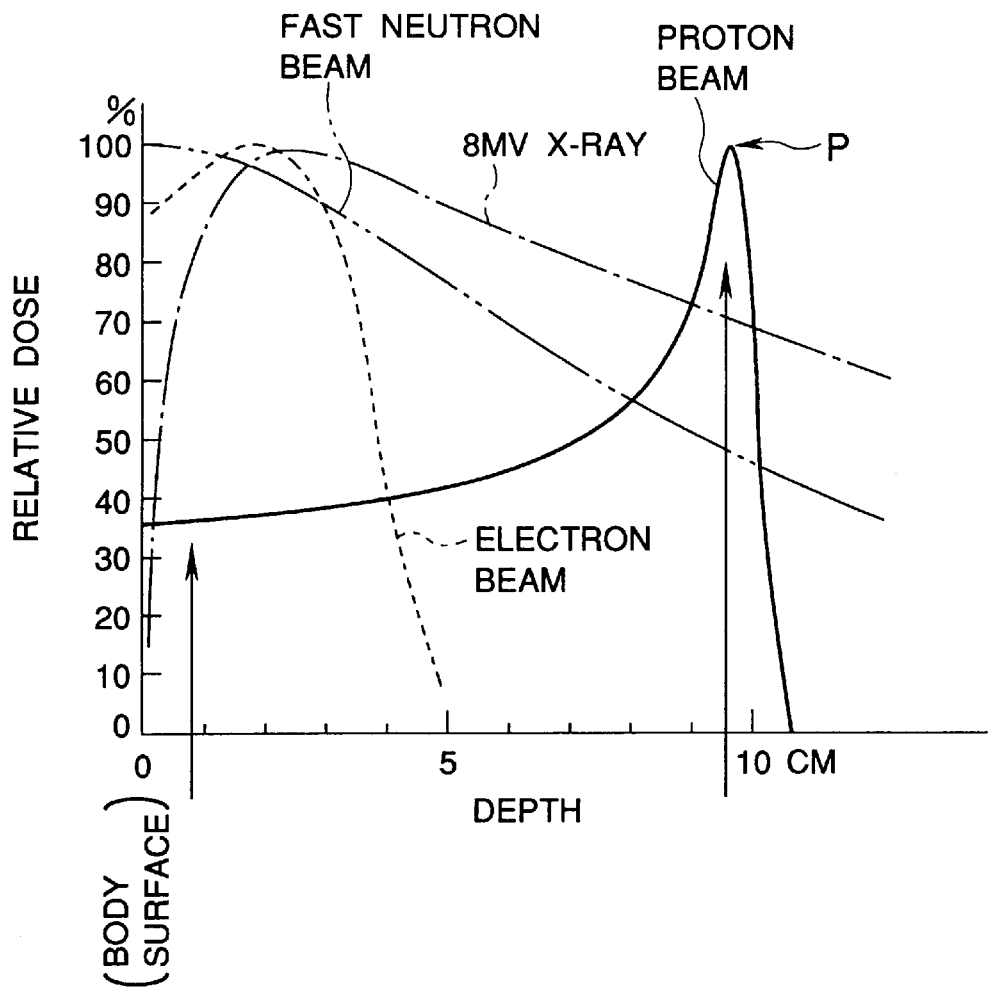
FIG. 14 is a diagrammatic view showing the comparison of the deep dose distributions in various radiation including proton beam.

As shown in FIGS. 12 and 13, the short isocentric axis (i-axis) 62 rotated around the Z-axis is provided on the bed platform 54, and further, the relative isocentric rotation drive mechanism 60 rotating the i-axis 62 by a pulse motor and reduction mechanism. The amount of rotation is decided by a rotation position command signal transmitted from the control system of the diseased part positioning device holding a patient, which causes the bed pedestal 64 installed to the tip of the i-axis 62 to be rotated θi degrees around the i-axis 62 parallel to the Z-axis. A rotation detector, like a rotary encoder, which detects a relative rotation angle to the bed platform 54 of the i-axis 62 can be provided on the relative isocentric rotation drive mechanism 60 to detect the rotation angle of the rotation shaft, allowing a relative isocentric rotation feedback control using rotation position signal from the rotation detector as a feedback signal.

As shown in FIG. 12, more specifically in FIG. 13, a hinge mechanism 130 is provided on the bed pedestal 64, and a hinge base 132 supporting the bed 20 on which a patient is placed is made to be rotated around the pitching axis (p-axis) on the bed pedestal 64. The amount of rotation is determined according to a rotation position instruction signal transmitted from the control system of the diseased part positioning device holding the patient. Reference numeral 134 is a p-axis motor for rotating the p-axis and consists of a pulse motor, and there is provided a rotary encoder 136 for detecting the rotation angles of the rotation shaft. The rotation angles of the rotation shaft can be detected by the rotary encoder in the p-axis control, and also a pitching angle rotation negative feedback control can be performed with rotation position command signals obtained from the rotary encoder as feedback signals. Of course, the p-axis is also equipped with a brake mechanism.

There is provided a r-axis motor 140 for making the bed 20 to be oscillating rotated to the rolling axis (r-axis) in the hinge base 132. A rotary encoder 142 detecting the rotation angle of the r-axis is attached to the r-axis motor 140. The bed pedestal 64 is equipped with a brake mechanism, so that the operation of the bed 20 can be fixed to the bed pedestal 64 in the case of emergency. A position command signal sent from the control system of the diseased part positioning device holding a patient makes the bed 20 rotated along the r-axis. In addition, a relative position to the hinge base 132 of the bed 20 is detected according to a signal from the rotary encoder 142, and also a rolling angle control based on the feedback similar to that of the slide base 34 can be performed according to the position signal obtained from the rotary encoder.

Basically, the bed 20 swings about the r-axis, but actually it can be made rotated about the r-axis with manual operation using a handle 78 provided on the tip of the bed 20. The amount of rotation is incremental with respect to the amount of rotation position obtained from the rotary encoder 142, and a rotary encoder 79 is provided on the shaft of the handle 78 in order to obtain the amount of the increment. The bed 20 is actually rotatably retained with a bearing 22 with respect to the r-axis. On the other hand, a gear mechanism 76 connects between a rotary shaft of the handle 78 and the r-axis supporting the bed 20, and a housing of the gear mechanism 76 is anchored to the bed 20. The gear mechanism 76 enables the bed 20 to be rotated freely with respect to the r-axis by rotating the handle 78, however, the handle 78 is not rotated even when the r-axis is rotated as a worm gear or the like is employed in this structure. Therefore, when the r-axis is rotated by the r-axis motor 140, the bed 20 is swung without rotation of the handle 76. There is provided an acceleration sensor 26 which detects the acceleration in the X-axis, Y-axis, and Z-axis directions, respectively.

The treatment table is generally constituted to be durable and substantially whole of the bed can be regarded as a rigid structure, and the position of the tip of the bed 20 on which each axis is connected and, moreover, a human body having a weight of several tens of kg is placed, position of the bed 20 that is the position of a diseased part, is lowered as compared with that of no-load condition of the bed 20, but the amount of distortion is simulated and is corrected when the patient is actually transferred to a predetermined position. Further, a fine vibration resulting from displacement caused by respiration of the human body during therapy may generate in the whole system of the treatment table, resulting in displacement of the diseased part. In the treatment table according to the present embodiment, the time constant of each axis with a no-load has been measured beforehand and stored as the known values. As a result, the entire number of vibration when weight of a human body is added to the bed 20 can be calculated with simulation. When the acceleration sensor 26 detects an acceleration in the X-axis, Y-axis, or Z-axis directions during therapy, vibration signals which are opposite in direction and equal in amplitude of the detected acceleration are added to each axis to hold the position of diseased part of a patient stationary.

In the present embodiment, all of the mechanisms are made to be electrically operated, but any of the mechanisms can be made to be operated manually.

The present invention is applied to a proton beam therapy device in the embodiment described above, however, it will be appreciated that the present invention is not limited to the device but can be applied to other radiation therapy devices such as an X-ray and electron beam therapy device.

What is claimed is:

1. A bed system for radiation therapy including a bed to hold a patient stationary when the radiation therapy treatment is performed by applying radiation irradiated from an irradiating section to a diseased part of the patient, the bed system comprising:

an x-axis direction parallel transfer means for moving the bed in an x-axis direction relative to the bed;

a z-axis direction parallel transfer means for moving the bed in a z-axis direction perpendicular to the x-axis direction;

a y-axis direction parallel transfer means for moving the bed in a y-axis direction relative to the bed, the y-axis direction being perpendicular to the x-axis and z-axis directions;

a relative isocentric rotation means for rotating the bed about an isocentric axis that designates a height direction of the patient;

a rolling a rotation means for rotating the bed about a rolling axis that designates a central axis of the patient; and a pitching rotation means for rotating the bed about a pitching axis perpendicular to the central axis of the patient.

2. The bed system as set forth in claim 1, wherein a center of the rotation of the rotation means is positioned in an irradiation chamber when the bed is inserted into the irradiation chamber.

3. The bed system as set forth in claim 2, further comprising a rotation gantry that enables the irradiating section to be rotated around the bed.

4. The bed system as set forth in claim 3, further comprising a base of the bed system provided in front of said rotation gantry.

5. The bed system as set forth in claim 1, wherein said rolling rotation means includes:

a hinge stand for rotating the bed about a central axis thereof;

the pitching rotation means includes a bed pedestal for rotating an end of the bed supported on the hinge stand in a longitudinal direction to incline a bed surface relative to a floor surface; and the relative isocentric rotation means includes a bed platform for supporting the bed pedestal for rotatably driving the bed pedestal in an X-Y plane direction.

6. The bed system as set forth in claim 5, wherein said rolling rotation means comprise a handle mechanism to rotate the bed manually about the central axis of the bed.

7. The bed system as set forth in claim 1, wherein said y-axis direction parallel transfer means comprises a Y-axis slide table for driving either one of the bed and the bed platform in the Y-axis direction;

the Z-axis direction parallel transfer means comprises a lift table for driving the Y-axis slide table in the Z-axis direction; and the X-axis direction parallel transfer means comprises a base for driving the lift table in the X-axis direction.

8. The bed system as set forth in claim 7, wherein said base is fixed to a bottom surface of a pit and on an upper surface of the pit is a caterpillar-like access floor which moves along with X-axis direction movement of the lift table and covers a pit opening on right and left sides of the lift table.

9. The bed system as set forth in claim 7, wherein said Z-axis direction parallel transfer means comprises a multi-step type telescopic cylinder.

10. The bed system as set forth in claim 7, further comprising brake mechanisms between any one of the hinge stand, the bed pedestal, the bed platform, the Y-axis slide table, the lift table, and the base along with their respective supporting sections.

11. The bed system as set forth in claim 1, further comprising an acceleration sensor which detects acceleration generated in any one of three dimensions is provided in the bed, there is also provided control means for issuing a drive command to said rotation means and parallel transfer means so that the rotation and parallel transfer means are each driven in a dimensional direction which decreases an output of the acceleration sensor.

12. The bed system as set forth in claim 7, wherein brake mechanisms of friction and fitting are provided between the lift table and the base.

13. The bed system as set forth in claim 7, wherein at least one of the rotation means and the parallel transfer means are driven with a negative feedback control which controls a command position and a present position so as to be always maintained in the same position.

* * * * *

UNITED STATES PATENT AND TRADEMARK OFFICE
CERTIFICATE OF CORRECTION

PATENT NO. : 6,094,760
DATED : August 1, 2000
INVENTOR(S) : Nonaka et al.

It is certified that error appears in the above-identified patent and that said Letters Patent is hereby corrected as shown below:

<u>Title page</u>,
Item [73], Assignee, please add a second Assignee's name and address as follows:
-- Obayashi Manufacturing Co., Ltd., Tokyo, Japan --.

Signed and Sealed this

Eighteenth Day of January, 2005

JON W. DUDAS
*Director of the United States Patent and Trademark Office*